United States Patent [19]

Martel et al.

[11] 4,431,576
[45] Feb. 14, 1984

[54] PERFUMANT CYCLOPROPANE-CARBOXYLIC ACID DERIVATIVES

[75] Inventors: Jacques Martel, Bondy; Jean Buendia, Le Perreux-sur-Marne; Francois Nezot, Thiais, all of France

[73] Assignee: Roussel Uclaf, Paris, France

[21] Appl. No.: 343,348

[22] Filed: Jan. 27, 1982

[30] Foreign Application Priority Data

Feb. 5, 1981 [FR] France .................... 81 02236

[51] Int. Cl.³ .................... A61K 7/46; C11B 9/00
[52] U.S. Cl. .................... 252/522 R; 252/174.11;
424/47; 424/49; 424/69; 424/70; 424/76;
260/464; 560/124; 549/66; 549/323
[58] Field of Search .................... 260/464; 424/47, 49,
424/69, 70, 76; 252/522 R, 174.11; 560/124

[56] References Cited

U.S. PATENT DOCUMENTS

| | | | |
|---|---|---|---|
| 3,766,218 | 10/1973 | Ueda et al. | 560/124 X |
| 4,217,300 | 8/1980 | Lantzsch | 560/124 X |
| 4,299,967 | 11/1981 | Dingwall et al. | 560/124 X |
| 4,310,540 | 1/1982 | Lantzsch et al. | 560/124 X |
| 4,327,109 | 4/1982 | Mizutani et al. | 560/124 X |
| 4,335,252 | 6/1982 | Engel | 560/124 |

OTHER PUBLICATIONS

*Perfume and Flavor Chemicals*, vol. I, No. 1187, Arctander (1969).
Kondo et al., CA 85: 78225b (1976).
Elliott et al., CA 82: 155439s (1975).
Nagase et al., CA 84: 179749k (1976).

*Primary Examiner*—Thomas A. Waltz
*Attorney, Agent, or Firm*—Hammond & Littell, Weissenberger and Muserlian

[57] ABSTRACT

A compound in all its possible isomeric forms and mixtures thereof of the formula

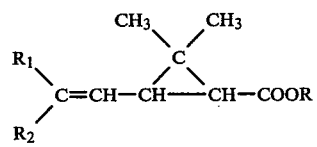

wherein R is selected from the group consisting of (a) alkyl of 1 to 12 carbon atoms optionally substituted with cycloalkyl or cycloalkenyl of 3 to 6 carbon atoms or a hydrocarbon chain of 2 to 8 carbon atoms optionally interrupted by an oxygen or ketone, (b) alkenyl and alkynyl of 3 to 8 carbon atoms, (c) cycloalkyl of 3 to 12 carbon atoms optionally containing at least one double bond and substituted with at least one alkyl and (d) aralkyl of 7 to 12 carbon atoms optionally substituted with at least one member of the group consisting of alkyl of 1 to 4 carbon atoms, alkoxy of 1 to 4 carbon atoms, halogen and —$CF_3$ and $R_1$ and $R_2$ are individually selected from the group consisting of hydrogen, —CHO, —$COAlK_1$, —$COOAlK_2$ and —CN, at least one being hydrogen, $AlK_1$ and $AlK_2$ are alkyl of 1 to 8 carbon atoms and $R_1$ and $R_2$ taken together with the carbon atom to which they are attached form the group

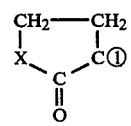

and X is selected from the group consisting of sulfur, oxygen and imino joined to the 1-carbon atom with a double bond with the proviso that the double bond has the E geometry when $R_1$ or $R_2$ are —CHO, —$COAlK_1$, —$COOAlK_2$ or

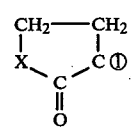

and their preparation and odorant compositions containing at least one compound of formula I as a prefume agent.

16 Claims, No Drawings

PERFUMANT CYCLOPROPANE-CARBOXYLIC ACID DERIVATIVES

STATE OF THE ART

Commonly assigned U.S. patent application Ser. No. 307,629, filed Oct. 1, 1981, now abandoned, describes cyclopropane carboxylic acid esters having in the 3-position an alkenyl group having perfume properties.

OBJECTS OF THE INVENTION

It is an object of the invention to provide the novel compounds of formula I in their various isomeric forms and mixtures thereof and a process for their preparation.

It is another object of the invention to provide novel odorant compositions and to a novel method of imparting a pleasant odor to a composition by incorporating into the composition an odorantly effective amount of at least one compound of formula I.

These and other objects and advantages of the invention will become obvious from the following detailed description.

THE INVENTION

The novel compounds of the invention are compounds in all its possible isomeric forms and mixtures thereof of the formula

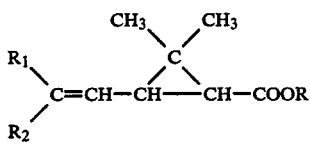

wherein R is selected from the group consisting of (a) alkyl of 1 to 12 carbon atoms optionally substituted with cycloalkyl or cycloalkenyl of 3 to 6 carbon atoms or a hydrocarbon chain of 2 to 8 carbon atoms optionally interrupted by an oxygen or ketone, (b) alkenyl and alkynyl of 3 to 8 carbon atoms, (c) cycloalkyl of 3 to 12 carbon atoms optionally containing at least one double bond and substituted with at least one alkyl and (d) aralkyl of 7 to 12 carbon atoms optionally substituted with at least one member of the group consisting of alkyl of 1 to 4 carbon atoms, alkoxy of 1 to 4 carbon atoms, halogen and —CF$_3$ and R$_1$ and R$_2$ are individually selected from the group consisting of hydrogen, —CHO, —COAlK$_1$, —COOAlK$_2$ and —CN, at least one being hydrogen, AlK$_1$ and AlK$_2$ are alkyl of 1 to 8 carbon atoms and R$_1$ and R$_2$ taken together with the carbon atom to which they are attached form the group

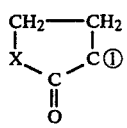

and X is selected from the group consisting of sulfur, oxygen and imino joined to the 1-carbon atom with a double bond with the proviso that the double bond has the E geometry when R$_1$ or R$_2$ are —CHO, —COAlK$_1$, —COOAlK$_2$ or

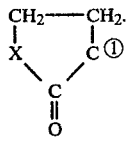

The compounds of formula I can exist in a number of possible isomeric forms as they possess two asymetric carbon atoms in the 1- and 3-positions of the cyclopropane ring and may also possess one or more asymetric centers or axes in the R portion of the molecule. They may also possess an isomery due to the double bond in the 3-side chain. All known processes to date only permit the good preparation of the products with E configuration on the level with the double bond except for the compounds when R$_1$ or R$_2$ is —CN.

AlK$_1$ and AlK$_2$ are preferably methyl, ethyl, n-propyl or isopropyl.

Examples of R are alkyl such as methyl, ethyl, n-propyl, isopropyl, butyl, tert.-butyl, isobutyl, n-pentyl, n-hexyl, n-heptyl, 2-methyl-pentyl, 2,3-dimethyl-butyl, 2-methyl-hexyl, 2,2-dimethyl-pentyl, 3,3-dimethyl-pentyl, 3-ethyl-pentyl, n-octyl, 2,2-dimethylhexyl, 3,3-dimethylhexyl, 3-methyl-3-ethyl-pentyl, nonyl, 2,4-dimethyl-heptyl and n-decyl; alkyl substituted with cycloalkyl, cycloalkenyl or hydrocarbon chain such as alkyl substituted with cyclopropyl, cyclopentyl, cyclohexyl, cyclohexenyl or cyclopentenyl; alkenyl such as butenyl, isobutenyl and crotonyl; alkynyl such as propynyl and butynyl; optionally unsaturated cycloalkyl such as cyclopropyl, cyclopentyl, cyclohexyl, cycloheptyl and cyclooctyl containing several double bonds and preferably 2 double bonds or substituted with at least one alkyl of 1 to 3 carbon atoms such as methyl, ethyl and n-propyl.

R may also be aralkyl such as benzyl or phenethyl optionally substituted in the m-, p- and/or o-positions with at least one member of the group consisting of alkyl and alkoxy of 1 to 4 carbon atoms such as methyl or methoxy, —CF$_3$ or a halogen such as chlorine or fluorine or a combination thereof.

Among the preferred compounds of formula I are those wherein the cyclopropane carboxylic acid moiety has the (1R,trans) or (1R,cis) structure, those wherein R is alkyl of 1 to 4 carbon atoms, those wherein R is benzyl, those wherein R$_1$ or R$_2$ is —CHO, those wherein R$_1$ or R$_2$ is —COCH$_3$ or —COOCH$_3$ and those wherein R$_1$ or R$_2$ is —CN.

Specific preferred compounds of formula I are ethyl (1R,cis) 2,2-dimethyl-3-[(E)-3-methoxy-3-oxo-propen-1-yl]-cyclopropane-1-carboxylate, benzyl (1R,cis) 2,2-dimethyl-3-[(E+Z)-2-cyano-ethenyl]-cyclopropane-1-carboxylate and methyl (1R,cis) 2,2-dimethyl-3-[(E)(-dihydro-2-oxo-3-(2H)-thienylidene)-methyl]-cyclopropane-1-carboxylate.

The novel process of the invention for the preparation of the compounds of formula I comprises reacting an acid of the formula

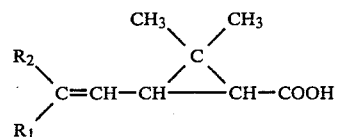

or a functional derivative thereof wherein $R_2$ and $R_1$ have the above definition with an alcohol of the formula $$R\text{—}OH \qquad \qquad III$$

or a functional derivative thereof wherein R has the above definition to obtain the corresponding compound of formula I.

Preferably the acid of formula II is reacting with the alcohol of formula III in the presence of dicyclohexylcarbodiimide or dicycloisopropylcarbodiimide although other classical methods for the formation of esters are equally useful. The preferred functional alcohol derivative has the formula

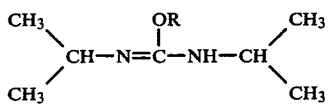

The functional derivative of the acid of formula II is the acid chloride or acid anhydride.

In a modification of the process of the invention for the preparation of a compound of formula I, a compound of the formula

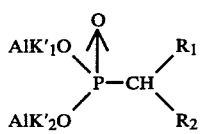

wherein $AlK'_1$ and $AlK'_2$ are alkyl of 1 to 4 carbon atoms and $R_1$ and $R_2$ have the above definition or a compound of the formula

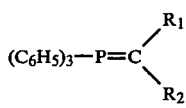

wherein $R_1$ and $R_2$ have the above definition, is subjected according to the Wittig reaction with an aldehyde of the formula

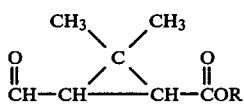

The novel odorant compositions of the invention are comprised of an odorantly effective amount of at least one compound of formula I and a carrier. The compositions have an agreeable odor such as a floral odor, a flowerly odor, a fresh odor, a spice odor or a woody odor.

The compositions may be used as odorants in perfumes or to prepare odorant compositions which serve as perfume bases. They are also useful in the preparation of hygienic compositions such as soaps, talcum powders, shampoos, dentifrices, bath salts, bath oils or bubble baths, deodorants or in the preparation of cosmetic products such as cremes, makeup milks, lotions, face paint, lipsticks and nail varnishes. The compositions may also be used in detergent compositions such as washing powders or the preparation of maintenance products such as waxes or the preparation of insecticides.

The compounds of formula I may be used to impart a pleasant odor to products lacking any odor or to raise up, exalt or modify the odor of compositions having their own odor. They may also be used to mask a disagreeable odor of a product. Naturally, the perfumes, hygienic products, cosmetics, detergent products and maintenance products are prepared by the usual techniques employed in these industries which are large described in the literature.

The compositions of the invention may contain other usual ingredients such as support vehicles, modifiers, fixing agents, preservatives, stabilizers and other ingredients such as supports, solvents, dispersants and emulsifiers usually used.

When the compounds of formula I are used in perfumes, other components well known in the perfumery art can be added to the compounds of formula I, which components may be natural products such as vetiver essence, cedar essence, bergamot orange essence, pine needle essence, lemon essence, jasmin or mandarin orange essence or may be synthetic products such as aldehydes commonly used in perfumery such as hydroxycitronella, ketones such as α-ionone, phenolic compounds such as eugenol, alcohols such as geraniol or lactones such as coumarine.

The amounts of the compounds of formula I used in perfumes will vary greatly as a function of the nature of the specific compound, the use one wishes to make, the intensity of the odor desired as well as, naturally, the nature and composition of the other ingredients added thereto. In perfumes, there may be used 0.1 to 10 parts by weight of the compounds of formula I per 100 parts by weight of the compositions and when used in a perfume base, the base may contain up to 20% by weight of the compound of formula I. When used in detergents, 0.1 to 2 parts by weight of the compounds of formula I per 100 parts by weight of the detergent composition may be used.

The normal method of the invention for imparting a pleasant odor to a composition comprises incorporating into a composition an odorantly effective amount of at least one compound of formula I.

In the following examples there are described several preferred embodiments to illustrate the invention. However, it should be understood that the invention is not intended to be limited to the specific embodiments.

The structures of the compounds of these following examples have, in each case, been confirmed by carrying out NMR spectra in deuterochloroform.

EXAMPLE 1

Methyl (1R,trans) 2,2-dimethyl-3-[(E)-2-formylethenyl]-cyclopropane-1-carboxylate STEP A: Triphenyl-1,3-dioxolan-2-yl-methyl bromide A mixture of 180 g of 2-(bromoethyl)-1,3-dioxolane and 260 g of triphenylphosphine was heated at 80° C. for 36 hours and was cooled. The resulting product was dissolved in methylene chloride and the solution was slowly poured into 3000 ml of ether. The mixture was stirred and was vacuum filtered and the product was empasted with ether to obtain 359 g of triphenyl-1,3-dioxolan-2-yl-methyl bromide melting at 206° C.

STEP B: Methyl (1R,trans) 2,2-dimethyl-3-[(E)-2-formylethenyl]-cyclopropane-1-carboxylate A solution of 17.1 ml of lithium methylate in methanol was added over 2½ hours at ≃75° C. to a solution of 46.8 g of methyl (1R,trans) 2,2-dimethyl-3-formyl-cyclopropane-1-carboxylate, 193.2 g of the product of Step A and 750 ml of dimethylformamide and the mixture was stirred at ≃75° C. for 5 hours and then stood overnight at room temperature. The mixture was poured with stirring into an ice-water mixture and the resulting mixture was extracted with ether. The organic phase was washed with aqueous saturated sodium chloride solution and dried under reduced pressure at 50° C. The residue was dissolved in a solution of 750 ml of tetrahydrofuran and 750 ml of N hydrochloric acid and the solution was stirred at room temperature for 3 hours and was poured into water. The mixture was extracted with ether and the organic phase was washed with aqueous solution bicarbonate solution, with aqueous saturated sodium chloride solution, was dried and evaporated to dryness. The residue was taken up in an 8-2 petroleum ether (b.p.=60°-80° C.)-ethyl acetate mixture and the mixture was vacuum filtered. The filtrate was evaporated to dryness and the residue was chromatographed over silica gel. Elution with an 8-2 petroleum ether-ethyl acetate mixture yielded 37.6 g of methyl (1R,trans) 2,2-dimethyl-3[(E)-2-formylethenyl]-cyclopropane-1-carboxylate with a refractive index of $n_D^{28} = 1.5018$.

EXAMPLE 2

Methyl (1R,trans) 2,2-dimethyl-3-[(E)-3-oxo-1-butenyl]-cyclopropane-1-carboxylate A mixture of 5 g of methyl (1R,trans) 2,2-dimethyl-3-formyl-cyclopropane-1-carboxylate, 11.3 g of 2-oxopropyl-triphenylphosphonium bromide and 50 ml of dichloroethane was refluxed for 2 hours and the temperature was allowed to return to room temperature. The mixture was evaporated to dryness under reduced pressure and the 19 g of oil residue were empasted with ether and filtered. The filtrate was evaporated to dryness and the 5 g of oil residue were chromatographed over silica gel. Elution with a 7-3 cyclohexane-ethyl acetate mixture yielded 4.46 g of methyl (1R,trans) 2,2-dimethyl-3-[(E)-3-oxo-1-butenyl]-cyclopropane-1-carboxylate with a specific rotation of $[\alpha]_D^{20} = +108° \pm 2.5°$ (c=0.6% in benzene).

EXAMPLE 3

Ethyl (1R,trans) 2,2-dimethyl-3[(E)-3-oxo-1-butenyl]-cyclopropane-1-carboxylate A mixture of 2 ml of pyridine, 2.9 g of (1R,trans) 2,2-dimethyl-3-[(E)-3-oxo-1-butenyl]-cyclopropane-1-carboxylic acid chloride, 1 ml of ethanol and 25 ml of benzene was stirred at 0° to 5° C. for 20 minutes and at room temperature for 2 hours and was then poured into iced aqueous N/6 hydrochloric acid solution. The mixture was extracted with ether and the organic phase was washed with water, dried and evaporated to dryness at 40° C. under reduced pressure. The 4.19 g of oil residue were chromatographed over silica gel and eluted with a 7-3 cyclohexane-ethyl acetate mixture to obtain 1.43 g of ethyl (1R,trans) 2,2-dimethyl-3-[(E)-3-oxo-1-butenyl]-cyclopropane-1-carboxylate with a specific rotation of $[\alpha]_D^{20} = +82° \pm 3°$ (c=0.5% in benzene).

EXAMPLE 4

Isopropyl (1R,trans) 2,2-dimethyl-3-[(E)-3-oxo-1-butenyl]-cyclopropane-1-carboxylate Using the procedure of Example 3, 2.9 g of (1R,trans) 2,2-dimethyl-3-[(E)-3-oxo-1-butenyl]-cyclopropane-1-carboxylic acid chloride and 1.15 ml of isopropanol were reacted to obtain 1.46 g of isopropyl (1R,trans) 2,2-dimethyl-3-[(E)-3-oxo-1-butenyl]-cyclopropane-1-carboxylate with a specific rotation of $[\alpha]_D^{20} = +63.5° \pm 3°$ (c=0.3% in benzene).

EXAMPLE 5

Tert.-butyl (1R,trans) 2,2-dimethyl-3-[(E)-3-oxo-1-butenyl]-cyclopropane-1-carboxylate Using the procedure of Example 3, 2.9 g of (1R,trans) 2,2-dimethyl-3-[(E)-3-oxo-1-butenyl]-cyclopropane-1-carboxylic acid chloride and 1.4 ml of tert.-butanol were reacted to obtain 1.43 g of tert.-butyl (1R,trans) 2,2-dimethyl-3-[(E)-3-oxo-1-butenyl]-cyclopropane-1-carboxylate with a specific rotation of $[\alpha]_D^{20} = +67° \pm 4°$ (c=0.25% in benzene).

EXAMPLE 6

Isopropyl (1R,cis) 2,2-dimethyl-3-[(E)-3-oxo-1-butenyl]-cyclopropane-1-carboxylate Using the procedure of Example 3, 6 g of (1R,cis) 2,2-dimethyl-3-[(E)-3-oxo-1-butenyl]-cyclopropane-1-carboxylic acid chloride and 2.7 ml of isopropanol were reacted to obtain 1.96 g of isopropyl (1R,cis) 2,2-dimethyl-3-[(E)-3-oxo-1-butenyl]-cyclopropane-1-carboxylate with a specific rotation of $[\alpha]_D^{20} = -39° \pm 5°$ (c=0.2% in benzene).

EXAMPLE 7

Methyl (1R,trans) 2,2-dimethyl-3-[(E)-3-methoxy-3-oxo-1-propenyl]-cyclopropane-1-carboxylate 20.3 ml of 0.5 m/l of diazomethane in methylene chloride were poured into a solution of 2.011 g of (1R,trans) 2,2-dimethyl-3-[(E)-3-methoxy-3-oxo-1-propenyl]-cyclopropane-1-carboxylic acid in 5 ml of methylene chloride and the mixture was stirred at 20° C. for 10 minutes. The methylene chloride was distilled off under reduced pressure and the 2.195 g of oil residue were chromatographed over silica gel. Elution with a 95-5 benzene-ethyl acetate mixture yielded 1.16 g of methyl (1R,trans) 2,2-dimethyl-3-[(E)-3-methoxy-3-oxo-1-propenyl]-cyclopropane-1-carboxylate with a specific rotation of $[\alpha]_D^{20} = +105° \pm 3°$ (c=0.5% in chloroform).

EXAMPLE 8

Isopropyl (1R,trans) 2,2-dimethyl-3-[(E)-3-methoxy-3-oxo-1-propenyl]-cyclopropane-1-carboxylate Using the procedure of Example 3, 2.7 g of (1R,trans) 2,2-dimethyl-3-[(E)-3-methoxy-3-oxo-1-propenyl]-cyclopropane-1-carboxylic acid chloride in benzene and 1 ml of isopropanol were reacted to obtain 1.7 g of isopropyl (1R,trans) 2,2-dimethyl-3-[(E)-3-methoxy-3- oxo-1-propenyl]-cyclopropane-1-carboxylate with a specific rotation of $[\alpha]_D^{20} = +84°$ (c=1.25% in chloroform).

EXAMPLE 9

Ethyl (1R,trans) 2,2-dimethyl-3-[(E)-3-methoxyl-3-oxo-1-propenyl]-cyclopropane-1-carboxylate Using the procedure of Example 3, 2.7 g of (1R,trans) 2,2-dimethyl-3-[(E)-3-methoxy-3-oxo-1-propenyl]-cyclopropane-1-carboxylic acid chloride in 12.5 ml of benzene and 1 ml of ethanol were reacted to obtain 1.31 g of ethyl (1R,trans) 2,2-dimethyl-3-[(E)-3-methoxy-3-oxo-1-propenyl]-cyclopropane-1-carboxylate with a specific rotation of $[\alpha]_D^{20} = +93° \pm 1.5°$ (c=1% in chloroform).

EXAMPLE 10

Tert.-butyl (1R,trans) 2,2-dimethyl-3-[(E)-3-methoxy-3-oxo-1-propenyl]-cyclopropane-1-carboxylate Using the procedure of Example 3, 2.7 g of (1R,trans) 2,2-dimethyl-3-[(E)-3-methoxy-3-oxo-1-propenyl]-cyclopropane-1-carboxylic acid chloride in 12.5 ml of benzene and 1.23 ml of tert.-butanol were reacted to obtain 1.05 g of tert.-butyl (1R,trans) 2,2-dimethyl-3-[(E)-3-methoxy-3-oxo-1-propenyl]-cyclopropane-1-carboxylate melting at 67° C. with a specific rotation of $[\alpha]_D^{20} = +75.5° \pm 2°$ (c=0.5% in chloroform).

EXAMPLE 11

Benzyl (1R,trans) 2,2-dimethyl-3-[(E)-3-methoxy-3-oxo-1-propenyl]-cyclopropane-1-carboxylate Using the procedure of Example 3, 12.5 ml of 1 M/l of (1R,trans) 2,2-dimethyl-3-[(E)-3-methoxy-3-oxo-1-propenyl]-cyclopropane-1-carboxylic acid chloride in benzene and 1.35 ml of benzyl alcohol were reacted to obtain 1.77 g of benzyl (1R,trans) 2,2-dimethyl-3[(E)-3-methoxy-3-oxo-1-propenyl]-cyclopropane-1-carboxylate with a specific rotation of $[\alpha]_D^{20} = +47.5° \pm 1.5°$ (c=1% in chloroform).

EXAMPLE 12

Methyl (1R,cis) 2,2-dimethyl-3-[(E)-3-methoxy-3-oxo-1-propenyl]-cyclopropane-1-carboxylate Using the procedure of Example 7, 1.26 g of (1R,cis) 2,2-dimethyl-3-[(E)-3-methoxy-3-oxo-1-propenyl]-cyclopropane-1-carboxylic acid and 12.7 ml of 0.5 M/l of diazomethane in methylene chloride were reacted to obtain 0.678 g of methyl (1R,cis) 2,2-dimethyl-3-[(E)-3-methoxy-3-oxo-1-propenyl]-cyclopropane-1-carboxylate with a specific rotation of $[\alpha]_D^{20} = -4° \pm 2°$ (c=0.6% in chloroform).

EXAMPLE 13

Ethyl (1R,cis) 2,2-dimethyl-3-[(E)-3-methoxy-3-oxo-1-propenyl]-cyclopropane-1-carboxylate Using the procedure of Example 3, 1.51 g of (1R,cis) 2,2-dimethyl-3-[(E)-3-methoxy-3-oxo-1-propenyl]-cyclopropane-1-carboxylic acid chloride in 10 ml of benzene and 0.465 ml of ethanol were reacted to obtain 0.837 g of ethyl (1R,cis) 2,2-dimethyl-3-[(E)-3-methoxy-3-oxo-1-propenyl]-cyclopropane-1-carboxylate with a specific rotation of $[\alpha]_D^{20} = -21° \pm 1.5°$ (c=1% in chloroform).

EXAMPLE 14

Isopropyl (1R,cis) 2,2-dimethyl-3-[(E)-3-methoxy-3-oxo-1-propenyl]-cyclopropane-1-carboxylate Using the procedure of Example 3, 1.51 g of (1R,cis) 2,2-dimethyl-3-[(E)-3-methoxy-3-oxo-1-propenyl]-cyclopropane-1-carboxylic acid chloride in benzene and 0.61 ml of isopropanol were reacted to obtain 0.820 g of isopropyl (1R,cis) 2,2-dimethyl-3-[(E)-3-methoxy-3-oxo-1-propenyl]-cyclopropane-1-carboxylate with a specific rotation of $[\alpha]_D^{20} = -28° \pm 1.5°$ (c=1% in chloroform).

EXAMPLE 15

Tert.-butyl (1R,cis) 2,2-dimethyl-3-[(E)-3-methoxy-3-oxo-1-propenyl]-cyclopropane-1-carboxylate Using the procedure of Example 3, 1.51 g of (1R,cis) 2,2-dimethyl-3-[(E)-3-methoxy-3-oxo-1-propenyl]-cyclopropane-1-carboxylic acid chloride in benzene and 0.754 ml of tert.-butanol were reacted to obtain 0.235 g of tert.-butyl (1R,cis) 2,2-dimethyl-3-[(E)-3-methoxy-3-oxo-1-propenyl]-cyclo-propane-1-carboxylate with a specific rotation of $[\alpha]_D^{20} = -23° \pm 1.5°$ (c=0.9% in chloroform).

EXAMPLE 16

Benzyl (1R,cis) 2,2-dimethyl-3[(E)-3-methoxy-3-oxo-1-propenyl]-cyclopropane-1-carboxylate Using the procedure of Example 3, 1.51 g of (1R,cis) 2,2-dimethyl-3-[(E)-3-methoxy-3-oxo-1-propenyl]-cyclopropane -1-carboxylic acid chloride in benzene and 0.83 ml of benzyl alcohol were reacted to obtain 1.046 g of benzyl (1R,cir) 2,2-dimethyl-3-[(E)-3-methoxy-3-oxo-1-propenyl]-cyclopropane-1carboxylate with a specific rotation of $[\alpha]_D^{20} = -56° \pm 1.5°$ (c=0.9% in chloroform).

EXAMPLE 17 Methyl (1R,trans) 2,2-dimethyl-3-[(E) (dihydro-2-oxo-3-(2H)-furanylidene)-methyl]-cyclopropane-1-carboxylate A mixture of 4.2 g of (1R,trans) 2,2-dimethyl-3-[(E) (dihydro-2-oxo-3-(2H)-furanylidene)-methyl]-cyclopropane-1-carboxylic acid, 3.5 g of methyl N,N'-diisopropyl-carbamimidate and about 20 ml of ethyl acetate was refluxed for 2 hours and was cooled and evaporated to dryness. The residue was chromatographed over silica gel and was eluted with a 6-4 cyclohexane-ethyl acetate mixture to obtain 2.5 g of methyl (1R,trans) 2,2-dimethyl-3-[(E) (dihydro-2-oxo-3-(2H)-furanylidene)-methyl]-cyclopropane-1-carboxylate with a specific rotation of $[\alpha]_D^{20} = +65° \pm 2.5°$ (c=0.6% in ethanol).

EXAMPLE 18

Methyl (1R,cis) 2,2-dimethyl-3-[(E) (dihydro-2-oxo-3-(2H)-furanylidene)-methyl]-cyclopropane-1-carboxylate Using the procedure of Example 17, 3.9 g of (1R,cis) 2,2-dimethyl-3-[(E) (dihydro-2-oxo-3-(2H)-furanylidene)-methyl]-cyclopropane-1-carboxylic acid and 3.5 g of methyl N,N'-diisopropylcarbamimidate were reacted to obtain 1.2 g of methyl (1R,cis) 2,2- dimethyl-3-[(E) (dihydro-2-oxo-3-(2H)-furanylidene)-methyl]-cyclopropane-1-carboxylate with a specific rotation of $[\alpha]_D^{20} = +43° \pm 2.5°$ (c=0.5% in ethanol).

EXAMPLE 19

Ethyl (1R,trans) 2,2-dimethyl-3-[(E) (dihydro-2-oxo-3-(2H)-furanylidene)-methyl]-cyclopropane-1-carboxylate Using the procedure of Example 17, 7.8 g of (1R,trans) 2,2-dimethyl-3-[(E) (dihydro-2-oxo-3(2H)-furanylidene)-methyl]-cyclopropane-1-carboxylic acid and 7 g of ethyl N,N'-diisopropylcarbamimidate were reacted to obtain 5 g of ethyl (1R,trans) 2,2-dimethyl-3-[(E) (dihydro-2-oxo-3-(2H)-furanylidene)-methyl]-cyclopropane-1-carboxylate with a specific rotation of $[\alpha]_D^{20} = +50° \pm 2°$ (c=0.5% in ethanol).

EXAMPLE 20

Ethyl (1R,cis) 2,2-dimethyl-3[(E) (dihydro-2-oxo-3-(2H)-furanylidene)-methyl]-cyclopropane-1-carboxylate Using the procedure of Example 17, 3.9 g of (1R,cis) 2,2-dimethyl-3-](E) (dihydro-2-oxo-3-(2H)-furanylidene)-methyl]-cyclopropane-1-carboxylic acid and 3.5 g of ethyl N,N'-diisopropylcarbamimidate were reacted to obtain 1 g of ethyl (1R,cis) 2,2-dimethyl-3[(E) (dihydro-2-oxo-3-(2H)-furanylidene)-methyl]-cyclopropane-1-carboxylate with a specific rotation of $[\alpha]_D^{20} = +29.5°$ (c=0.6% in ethanol).

EXAMPLE 21

Isopropyl (1R,trans) 2,2-dimethyl-3-[(E) (dihydro-2-oxo-3-(2H)-furanylidene)-methyl]-cyclopropane-1-carboxylate Using the procedure of Example 17, 4 g of (1R,trans) 2,2-dimethyl-3-[(E) (dihydro-2-oxo-3(2H)-furanylidene)-methyl]-cyclopropane-1-carboxylic acid and 5 ml of isopropyl N,N'-diisopropylcarbamimidate were reacted to obtain 3.5 g of isopropyl (1R,trans) 2,2-dimethyl-3-[(E) (dihydro-2-oxo-3-(2H)-furanylidene)-methyl]-cyclopropane-carboxylate with a specific rotation of $[\alpha]_D^{20} = +38.5° \pm 1.5°$ (c=1% in ethanol).

EXAMPLE 22

Isopropyl (1R,cis) 2,2-dimethyl-3-[(E) (dihydro-2-oxo-3-(2H)-furanylidene)-methyl]-cyclopropane-1-carboxylate Using the procedure of Example 17, 8.4 g of (1R,cis) 2,2-dimethyl-3-[(E) (dihydro-2-oxo-3-(2H)-furanylidene)-methyl]-cyclopropane-1-carboxylic acid and 7.45 g of isopropyl N,N'-diisopropylcarbamimidate were reacted to obtain 4.96 g of isopropyl (1R,cis) 2,2-dimethyl-3-[(E) (dihydro-2-oxo-3-(2H)-furanylidene)-methyl]-cyclopropane-1-carboxylate with a specific rotation of $[\alpha]_D^{20} = +41° \pm 2.5°$ (c=0.5% in benzene).

EXAMPLE 23 Methyl (1R,trans) 2,2-dimethyl-3-[(E) (dihydro-2-oxo-3-(2H)-thienylidene)-methyl-cyclopropane-1-carboxylate Using the procedure of Example 17, 4.5 g of (1R,trans) 2,2-dimethyl-3-[(E) (dihydro-2-oxo-3-(2H)-thienylidene)-methyl]-cyclopropane-1-carboxylic acid and 3.5 g of methyl N,N'-diisopropylcarbamimidate were reacted to obtain 2.2 g of methyl (1R,trans) 2,2-dimethyl-3-[(E) (dihydro-2-oxo-3-(2H)-thienylidene)-methyl]-cyclopropane-1-carboxylate with a specific rotation of $[\alpha]_D^{20} = +66.5° \pm 1.5°$ (c=1.2% in ethanol).

EXAMPLE 24

Methyl (1R,trans) 2,2-dimethyl-3-[(E) (dihydro-2-oxo-3-(2H)-thienylidene)-methyl]-cyclopropane-1-carboxylate Using the procedure of Example 17, 4 g of (1R,trans) 2,2-dimethyl-3-[(E) (dihydro-2-oxo-3-(2H)-thienylidene)-methyl]-cyclopropane-carboxylic acid and 3.5 g of methyl N,N'-diisopropylcarbamimidate were reacted to obtain 0.8 g of methyl (1R,trans) 2,2-dimethyl-3-[(E) (dihydro-2-oxo-3-(2H)-thienylidene)-methyl]-cyclopropane-1-carboxylate with a specific rotation of $[\alpha]_D^{20} = +63.5° \pm 1.5°$ (c=1.1% in ethanol).

EXAMPLE 25

Ethyl (1R,cis) 2,2-dimethyl-3-[(E) (dihydro-2-oxo-3-(2H)-thienylidene)-methyl]-cyclopropane-1-carboxylate Using the procedure of Example 17, 9 g of (1R,cis) 2,2-dimethyl-3-[(E) (dihydro-2-oxo-3-(2H)-thienylidene)-methyl]-cyclopropane-1-carboxylic acid and 7 g of ethyl N,N'-diisopropylcarbamimidate were reacted to obtain 4.5 g of ethyl (1R,cis) 2,2-dimethyl-3-[(E) (dihydro-2-oxo-3-(2H)-thienylidiene)-methyl]-cyclopropane-1-carboxylate with a specific rotation of $[\alpha]_D^{20} = +77° \pm 1.5°$ (c=1% in benzene).

EXAMPLE 26

Tert.-butyl (1R,trans) 2,2-dimethyl-3-[(E) (dihydro-2-oxo-3-(2H)-thienylidene)-methyl]cyclopropane-1-carboxylate Using the procedure of Example 17, 4.5 g of (1R,trans) 2,2-dimethyl-3-[(E) (dihydro-2-oxo-3-(2H)-thienylidene)-methyl]-cyclopropane-1-carboxylic acid and 5 g of tert.-butyl N,N'-diisopropylcarbamimidate were reacted to obtain 0.9 g of tert.-butyl (1R,trans) 2,2-dimethyl-3-dimethyl-3-[(E) (dihydro-2-oxo-3 -(2H)-thienylidene)-methyl]-cyclopropane-1-carboxylate with a specific rotation of $[\alpha]_D^{20} = +26° \pm 2° \pm 2°$ (c=0.7% in ethanol).

EXAMPLE 27

Isopropyl (1R,cis) 2,2-dimethyl-3-[(E) (dihydro-2-oxo-3-(2H)-thienylidene)-methyl]-cyclopropane-1-carboxylate Using the procedure of Example 17, 4.5 g of (1R,trans) 2,2-dimethyl-3-[(E) (dihydro-2-oxo-3-(2H)-(thienylidene)-methyl]-cyclopropane-1-carboxylic acid and 5 ml of isopriopyl N,N'-diisopropylcarbamimidate were reacted to obtain 3.8 g of isopropyl (1R,cis) 2,2-dimethyl-3-[(E) (dihydro-2-oxo-3-(2H)-thienylidene)-methyl]-cyclopropane-1-carboxylate with a specific rotation of $[\alpha]_D^{20} = +57°$ (c=1% in benzene).

EXAMPLE 28

Methyl (1R,cis) 2,2-dimethyl-3-[(E) (dihydro-2-oxo-3-(2H)-thienyledene)-methyl]-cyclopropane-1carboxylate Using the procedure of Example 17, 4.5 g of (1R,cis) 2,2-dimethyl-3-[(E) (dihydro-2-oxo-3-(2H)-thienylidene)-methyl]-cyclopropane-1-carboxylic acid and 3.5 g of methyl N,N'-diisopropylcarbamimidate were reacted to obtain 2.2 g of methyl (1R,cis) 2,2-dimethyl-3-[(E) (dihydro-2-oxo-3-(2H)-thienylidene)- methyl]-cyclopropane-1-carboxylate with a specific rotation of $[\alpha]_D^{20} = +63.5° \pm 1.5°$ (c=1.1% in ethanol).

EXAMPLE 29

Methyl (1R,cis) 2,2-dimethyl-3-[(Z)-2-cyanoethenyl]-cyclopropane-1-carboxylate 1.85 g of (1R,cis) 2,2-dimethyl-3-[(Z)-cyanoethenyl]-cyclopropane-1-carboxylic acid chloride were added at 0° to solution of 2 ml of methanol, 10 ml of benzene and 1 ml of pyridine and the reaction solution was stirred at 20° C. for 16 hours and was poured into water. The mixture was extracted with benzene and the organic phase was dried and evaporated to dryness under reduced pressure. The residue was chromatographed over silica gel and eluted with benzene to obtain 0.511 g of methyl (1R,cis) 2,2-dimethyl-3[(Z)-2-cyanoethenyl]-cyclopropane-1-carboxylate.

NMR Spectrum (deuterochloroform):
Peaks at 1.3 ppm (hydrogens of geminal methyls); at 3.7 ppm (hydrogens of methyl α to CO); at 1.95–2. ppm (hydrogen of 1-carbon of cyclopropane); at 2.18 to 2.5 ppm (hydrogen of 3-carbon of cyclopropane); at 5.3–5.48 ppm (hydrogens of 2-carbon of ethenyl); at 6.8–6.9–7.0 ppm (hydrogen of 1-carbon of ethenyl).

EXAMPLE 30

Ethyl (1R,trans) 2,2-dimethyl-3-[(E+Z)-2-cyano-ethenyl]-cyclopropane-1-carboxylate A mixture of 2 g of (1R, trans) 2,2-dimethyl-3-[(E+Z)-2-cyano-ethenyl]-cyclopropane-1-carboxylic acid, 50 ml of methylene chloride, 300 mg of 4-dimethylamino-pyridine and 2.5 g of dicyclohexycarbodiimide was stirred at 20° C. for 30 minutes and 1 ml of ethanol was added thereto. The mixture was stirred at 20° C. for 16 hours and was filtered. The filtrate was washed with aqueous 0.1N hydrochloric acid solution, with water, dried and evaporated to dryness under reduced pressure. The residue was chromatographed over silica gel and was eluted with a 95-5 toluene-ethyl acetate mixture to obtain 0.842 g of ethyl (1R, trans) 2,2-dimethyl-3-[(E+Z)-2-cyano-ethenyl]-cyclopropane-1-carboxylate with a specific rotation of $[\alpha]_D^{20} = +46° \pm 2.5°$ (c=0,6% in chloroform).

EXAMPLE 31

Methyl (1R, trans) 2,2-dimethyl-3-[(E+Z)-2-cyano-ethenyl]-cyclopropane-1-carboxylate A mixture of 1.6 g of a 60% sodium hydride suspension in oil and 60 ml of tetrahydrofuran was stirred at 20° C. and 7.09 g of 0,0-diethyl cyano-ethyl phosphonate were added over 30 minutes at 10° to 25° C. to the mixture. The mixture was stirred at 20° C. for one hour and then was cooled to −15° C. after which a solution of 3.12 g of methyl (1R, trans) 2,2-dimethyl-3-formyl-cyclopropane-1-carboxylate in 15 ml of tetrahydrofuran was added thereto. The solution was stirred at −15° C. for 2 hours and for one hour at 20° C. and was poured into a mixture of ice and 0.1N hydrochloric acid. The mixture was extracted with methylene chloride and the organic phase was washed with water until the wash water was neutral, was dried and evaporated to dryness. The residue was chromatographed over silica gel and was eluted with a 95-5 benzene-ethyl acetate mixture to obtain 2.04 g of methyl (1R, trans) 2,2-dimethyl-3-[(E+Z)-2-cyano-ethenyl]-cyclopropane-1-carboxylate with a specific rotation of $[\alpha]_D^{20} = +77° \pm 1.5°$ (c=1% in chloroform).

EXAMPLE 32

Benzyl (1R, trans) 2,2-dimethyl-3[(Z and E)-2-cyano-ethenyl]-cyclopropane-1-carboxylate Using the procedure of Example 30, 2 g of (1R, trans) 2,2-dimethyl-3-[(Z+E)-2-cyano-ethenyl]-cyclopropane-1-carboxylic acid and 2 ml of benzyl alcohol was reacted to obtain 2.9 g of product which were chromatographed over silica gel. Elution with a 95-5 toluene-ethyl acetate mixture yielded 700 mg of the Z isomer of benzyl (1R, trans) 2,2-dimethyl-3-[-2-cyano-ethenyl]-cyclopropane-1-carboxylate and 646 g of the E isomer. The Z isomer had a melting point of 64° C. and a specific rotation of $[\alpha]_D^{20} = -51.5° \pm 1.5°$ (c=1% in chloroform) and the E isomer had a specific rotation of $[\alpha]_D^{20} = +61° \pm 2.5°$ (c=0.5% in chloroform).

EXAMPLE 33

Isopropyl (1R, trans) 2,2-dimethyl-3-[(Z+E)-2-cyano-ethenyl]-cyclopropane-1-carboxylate Using the procedure of Example 30, 2 g of (1R, trans) 2,2-dimethyl-3-[(Z+E)-2-cyano-ethenyl]-cyclopropane-1-carboxylic acid and 1.3 ml of isopropanol were reacted to obtain 1.428 g of isopropyl (1R, trans) 2,2-dimethyl-3-[(Z+E)-2-cyano-ethenyl]-cyclopropane-1-carboxylate with a specific rotation of $[\alpha]_D^{20} = +48.5° \pm 1°$ (c=1% in chloroform).

EXAMPLE 34

Ethyl (1R, cis) 2,2-dimethyl-3-[(Z+E)-2-cyano-ethenyl]-cyclopropane-1-carboxylate Using the procedure of Example 30, 1.65 g of (1R, cis) 2,2-dimethyl-3-[(Z+E)-2-cyano-ethenyl]-cyclopropane-1-carboxylic acid and 2 ml of ethanol were reacted to obtain 1.187 g of ethyl (1R, cis) 2,2-dimethyl-3-[(Z+E)-2-cyano-ethenyl]-cyclopropane-1-carboxylate with a specific rotation of $[\alpha]_D^{20} = +44.5° \pm 2°$ (c=0.6% in chloroform).

EXAMPLE 35

Isopropyl (1R, cis) 2,2-dimethyl-3-[(Z+E)-2-cyano-ethenyl]-cycylopropane-1-carboxylate Using the procedure of Example 30, 1.6 g of (1R, cis) 2,2-dimethyl-3-[(Z+E)-2-cyano-ethenyl]-cyclopropane-1-carboxylic acid and 1 ml of isopropanol were reacted to obtain 1.275 g of isopropyl (1R, cis) 2,2-dimethyl-3[(Z+E)-2-cyano-ethenyl]-cyclopropane-1-carboxylate with a specific rotation of $[\alpha]_D^{20} = +34.5° \pm 1.5°$ (c=1% in chloroform).

EXAMPLE 36

Benzyl (1R, cis) 2,2-dimethyl-3-[(Z+E)-2-cyano-ethenyl]-cyclopropane-1-carboxylate Using the procedure of Example 30, 1.6 g of (1R, cis) 2,2-dimethyl-3-[(Z+E)-2-cyano-ethenyl]-cyclopropane-1-carboxylic acid and 1.5 ml of benzyl alcohol were reacted to obtain 1.73 g of benzyl (1R, cis) 2,2-dimethyl-3-[(Z+E)-2-cyano-ethenyl]-cyclopropane-1- carboxylate with a specific rotation of $[\alpha]_D^{20} = +12.5° \pm 3°$ (c=0.25% in chloroform).

EXAMPLE 37

A "rose" composition was prepared containing the following ingredients (parts by weight): 100 parts of the product of Example 36, 15 parts of Alpha Ionone, 15 parts of Aldehyde C 9 I/10 PDG, 15 parts of musk ketone, 30 parts of Benjoin resinoid, 40 parts of citronella acetate, 60 parts of bourbon Rhodine, 170 parts of phenethanol; 15 parts of methylionone, 15 parts of Nerol, 45 parts of geranyl acetate, 300 parts of citronellal and 180 parts of terpene-free geranium.

An "Opoponax" composition was prepared with the following ingredients (parts by weight): 100 parts of the product of Example 36, 310 parts of bergamot orange, 20 parts of synthetic Neroli, 10 parts of iron-free patchouli, 10 parts of rose essence, 60 parts of Vetiverol, 125 parts of Sandalol, 40 parts of castoreum resinoid, 80 parts of coumarine, 75 parts of gamma methylionone, 40 parts of vanilla, 25 parts of benjoin resinoid, 40 parts of musk ketone and 65 parts of musk Ambrette.

A "Jasmine" composition was prepared with the following ingredients (parts by weight): 100 parts of the product of Example 13, 260 parts of benzyl acetate, 60 parts of linalyl acetate, 60 parts of phenethanol, 90 parts of hexylcinnamic aldehyde, 60 parts of hydroxy citronnellal, 50 parts of benzyl salicylate, 30 parts of methyl anthranylate, 45 parts of Linalol, 15 parts of p-cresyl phenylacetate, 50 parts of extra ylang, 30 parts of sandalwood, 15 parts of dimethylbenzyl carbinol, 50 parts of styrax hyper essence and 85 parts of hedione.

EXAMPLE 38

Toilet soaps were prepared containing 5 parts by weight of the product of Example 1 per 1000 parts by weight of a commercial soap paste.

A commercial powdered detergent was also prepared containing 1 part of the product of Example 28 per 1000 parts of the detergent.

EXAMPLE 39

| Compound of Example | odor given off |
| --- | --- |
| 1 | iris |
| 36 | tutti fruity (mixture of fruits) |
| 13 | heady flowery |
| 28 | note of agrumes, grape fruit |

Various modifications of the products and process of the invention may be made without departing from the spirit or scope thereof and it is to be understood that the invention is intended to be limited only as defined in the appended claims.

What we claim is:

1. A perfumant composition containing as a perfumery agent an odorantly effective amount of at least one compound in all its possible isomeric forms and mixtures thereof of the formula

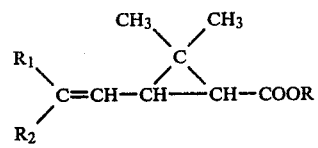

wherein R is selected from the group consisting of (a) alkyl of 1 to 12 carbon atoms optionally substituted with cycloalkyl or cycloalkenyl of 3 to 6 carbon atoms or a hydrocarbon chain of 2 to 8 carbon atoms optionally interrupted by an oxygen or ketone, (b) alkenyl and alkynyl of 3 to 8 carbon atoms, (c) cycloalkyl of 3 to 12 carbon atoms optionally containing at least one double bond and substituted with at least one alkyl and (d) aralkyl of 7 to 12 carbon atoms optionally substituted with at least one member of the group consisting of alkyl of 1 to 4 carbon atoms, alkoxy of 1 to 4 carbon atoms, halogen and $-CF_3$ and $R_1$ and $R_2$ are individually selected from the group consisting of hydrogen, $-CHO$, $-COAlK_1$, $-COOAlK_2$ and CN, with only one being hydrogen, $AlK_1$ and $AlK_2$ are alkyl of 1 to 8 carbon atoms and $R_1$ and $R_2$ taken together with the carbon atom to which they are attached form the group

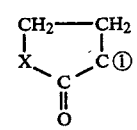

and X is selected from the group consisting of sulfur, oxygen and imino joined to the 1-carbon atom with a double bond with the proviso that the double bond has the E geometry when $R_1$ or $R_2$ are $-CHO$, $-COAlK_1$, $-COOAlK_2$ or

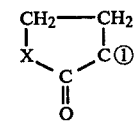

and at least one member of the group consisting of support vehicles, modifiers, fixing agents, preservatives, stabilizers, supports, solvents, dispersants and emulsifiers.

2. A composition of claim 1 wherein the cyclopropane carboxylic acid moiety has the (1R, trans) or (1R, cis) structure.

3. A composition of claim 1 or 2 wherein R is alkyl of 1 to 4 carbon atoms.

4. A composition of claim 1 or 2 wherein R is benzyl.

5. A composition of claim 1 or 2 wherein $R_1$ or $R_2$ is $-CHO$.

6. A composition of claim 1 or 2 wherein $R_1$ or $R_2$ is

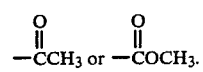

7. A composition of claim 1 or 2 wherein $R_1$ or $R_2$ is $-CN$.

8. A composition of claim 1 wherein the perfumary agent is selected from the group consisting of ethyl (1R, cis) 2,2-dimethyl-3-[(E)-3-methoxy-3-oxo-propen-1-yl]-cyclopropane-1-carboxylate, benzyl (1R, cis) 2,2-dimethyl-3-[(E+Z)-2-cyano-ethenyl]-cyclopropane-1-carboxylate and methyl (1R, cis) 2,2-dimethyl-3-[(E) (dihydro-2-oxo-3- (2H)-thienylidene)-methyl]-cyclopropane-1-carboxylate.

9. A method of imparting a pleasant odor to a composition comprising incorporating into the composition an odorantly effective amount of at least one compound

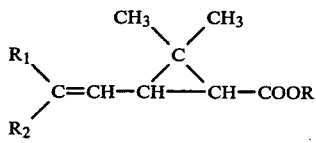

wherein R is selected from the group consisting of (a) alkyl of 1 to 12 carbon atoms optionally substituted with cycloalkyl or cycloalkenyl of 3 to 6 carbon atoms or a hydrocarbon chain of 2 to 8 carbon atoms optionally interrupted by an oxygen or ketone, (b) alkenyl and alkynyl of 3 to 8 carbon atoms, (c) cycloalkyl of 3 to 12 carbon atoms optionally containing at least one double bond and substituted with at least one alkyl and (d) aralkyl of 7 to 12 carbon atoms optionally substituted with at least one member of the group consisting of alkyl of 1 to 4 carbon atoms, alkoxy of 1 to 4 carbon atoms, halogen and —CF$_3$ and R$_1$ and R$_2$ are individually selected from the group consisting of hydrogen, —CHO, —COAlK$_1$, —COOAlK$_2$ and —CN, only one being hydrogen, AlK$_1$ and AlK$_2$ are alkyl of 1 to 8 carbon atoms and R$_1$ and R$_2$ taken together with the carbon atom to which they are attached form the group

```
   CH2————CH2
   |        |
   X        C①
    \      /
     C
     ||
     O
``` and X is selected from the group consisting of sulfur, oxygen and imino joined to the 1-carbon atom with a double bond with the proviso that the double bond has the E geometry when R$_1$ or R$_2$ are —CHO, —COAlK$_1$, —COOAlK$_2$ or

```
   CH2————CH2.
   |        |
   X        C①
    \      /
     C
     ||
     O
```

10. A method of claim 9 wherein the cyclopropane carboxylic acid moiety has the (1R, trans) or (1R, cis) structure.

11. A method of claim 9 wherein R is alkyl of 1 to 4 carbon atoms.

12. A method of claim 9 wherein R is benzyl

13. A method of claim 9 wherein R$_1$ or R$_2$ is —CHO.

14. A method of claim 9 wherein R$_1$ or R$_2$ is

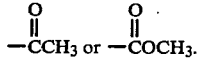

15. A method of claim 9 wherein R$_1$ or R$_2$ is —CN.

16. A method of claim 9 wherein the perfumary agent is selected from the group consisting of ethyl (1R, cis) 2,2-dimethyl-3-[(E)-3-methoxy-3-oxo-propen-1-yl]-cyclopropane-1-carboxylate, benzyl (1R, cis) 2,2-dimethyl-3-[(E+Z)-2-cyano-ethenyl]-cyclopropane-1-carboxylate and methyl (1R, cis) 2,2-dimethyl-3-[(E) (dihydro-2-oxo-3-(2H)-theinylidene)-methyl]-cyclopropane-1-carboxylate.

* * * * *